United States Patent [19]

Clark

[11] 4,221,224

[45] Sep. 9, 1980

[54] NON-AIRTIGHT PULMONARY MEASURING DEVICE

[75] Inventor: Justin S. Clark, Salt Lake City, Utah

[73] Assignees: Intermountain Health Care; Primary Children's Medical Center, both of Salt Lake City, Utah

[21] Appl. No.: 920,167

[22] Filed: Jun. 29, 1978

[51] Int. Cl.³ .............................................. A61B 5/08
[52] U.S. Cl. ..................................... 128/718; 128/725
[58] Field of Search ................... 128/2 A, 2.07–2.08, 128/718–719, 725; 422/83–84, 98; 73/421.5 R; 364/414–415

[56] References Cited

U.S. PATENT DOCUMENTS

| 3,507,146 | 4/1970 | Webb | 128/2.07 |
| 3,533,398 | 10/1970 | Jones | 128/2.07 |
| 3,659,590 | 5/1972 | Jones et al. | 128/2.08 |
| 3,666,955 | 5/1972 | Suprenant et al. | 128/2.08 |
| 3,785,370 | 1/1974 | Richards et al. | 128/2.08 |
| 3,896,792 | 7/1975 | Vail et al. | 128/2.07 |
| 3,910,261 | 10/1975 | Ragsdale et al. | 128/2.07 |
| 3,927,670 | 12/1975 | Turney et al. | 128/2.08 |
| 4,034,743 | 7/1977 | Greenwood et al. | 128/2.08 |
| 4,083,367 | 4/1978 | Portner et al. | 128/2.07 |

OTHER PUBLICATIONS

Ray, C. D., "Medical Engineering," pp. 326, 336, Yearbook Publ. Chic., 1974.

Primary Examiner—Robert W. Michell
Assistant Examiner—Francis J. Jaworski
Attorney, Agent, or Firm—Criddle & Western

[57] ABSTRACT

A non-airtight method for determining alveolar ventilation, oxygen uptake and carbon dioxide production which comprises introducing a known amount of an inert gas into the airway of a patient during inspiration and monitoring the expired gas until a steady state is reached wherein the volume of inert gas inhaled is equal to the amount exhaled and subsequently monitoring the expired air containing a known volume of inert gas for inert gas, carbon dioxide and oxygen concentrations.

17 Claims, 1 Drawing Figure

NON-AIRTIGHT PULMONARY MEASURING DEVICE

BACKGROUND OF THE INVENTION

This invention relates to a method of determining alveolar ventilation, carbon dioxide production and oxygen uptake. More particularly, this invention relates to a non-airtight method of determining the volume of alveolar gases and of carbon dioxide production and oxygen uptake of a human being.

Existing methods for making measurement of oxygen uptake and carbon dioxide production require an airtight connection to the patient for monitoring expired gas volume and concentration. In most cases an airtight seal in the form of a mask or nosepiece interconnects the patient with a bag, spirometer or other collection device from which the volume of gas can be measured and the concentration of oxygen and carbon dioxide determined.

Many patients, particularly infants and young children, will not tolerate such obtrusive interfacing to the monitoring equipment. In order to avoid direct interfacing to a patient other methods have been devised. One such method involves keeping a patient in a sealed box so there can be no undetected escape of expired gas. This method is bulky and too expensive to use for practical purposes other than as a research tool.

There are various methods used for collecting alveolar gas and determining its contents but all are dependent upon an airtight connection to the patient.

OBJECTS AND SUMMARY OF THE INVENTION

It is an object of the present invention to provide a method for determining alveolar ventilation, carbon dioxide production and oxygen uptake in a patient which does not require an airtight connection between the patient and the monitoring equipment.

it is also an object of this invention to provide a method for measuring alveolar ventilation, carbon dioxide production and oxygen uptake in a patient by non-airtight means using an inert tracer gas.

A further object of this invention is to provide a method for measuring alveolar ventilation, carbon dioxide production and oxygen uptake in a patient who will not tolerate an airtight interfacing connection.

A still further object of the present invention is to provide a method of determining alveolar volume and the production or uptake of critical gases by means not requiring an airtight seal between the patient and the monitoring equipment wherein a known volume and concentration of an inert gas inserted into the airway of a patient is used as a standard against which the quantities of the monitored gases may be determined.

These and other objects may be determined by injecting a known amount of an inert tracer gas, such as helium, as a bolus into the airway of a patient synchronous with inspiration such that all of the inert gas is carried into the alveolar compartments of the lungs. The tracer gas injected during inspiration and the tracer gas expired is monitored during the respiratory cycle until a steady state is reached in which the amount of tracer gas injected in each inspiratory phase equals the amount of tracer gas subsequently expired. The concentration of tracer gas expired can be monitored along with the concentrations of carbon dioxide and oxygen. Since the amount and concentration of tracer gas in the expired gas is known, the volume of gas expired may be determined. With the volume of expired gas known and the concentrations of carbon dioxide and oxygen in both expired and inspired gases being known it is possible to monitor and determine oxygen uptake and carbon dioxide production.

DETAILED DESCRIPTION OF THE INVENTION

Figure 1:
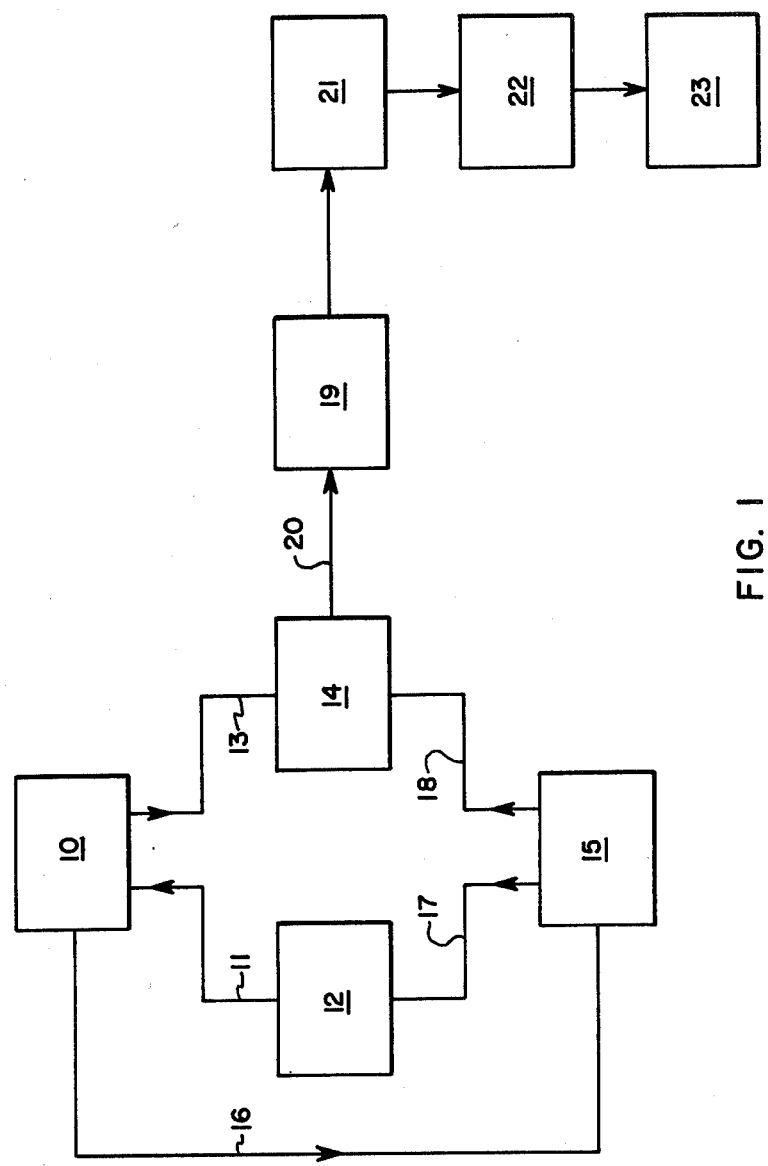
FIG. 1 is a block diagram of the system used in monitoring and determining alveolar ventilation, carbon dioxide production and oxygen uptake.

The key problem solved by the present invention is the ability to determine alveolar ventilation ($V_A$) without resorting to the use of an air tight connection between the patient and the monitoring equipment. Once $V_A$ is known other parameters such as carbon dioxide production ($\dot{V}_{CO_2}$) and oxygen uptake ($\dot{V}_{O_2}$) can be determined from monitoring $CO_2$ and $O_2$ concentrations in inspired and expired gases. Since the $CO_2$ concentration in ambient air is essentially zero and the $O_2$ concentration is known only the expired gases need to be monitored.

The alveolar ventilation can be determined using an inert gas, which is substantially insoluble in blood, such as helium, as a tracer. Known amounts of helium are inserted into the airway of a patient during inspiration utilizing rapidly responding injection means. Preferably the mode used is to attach a catheter to a noseclip and inject the inert tracer gas into one nostril of a patient. The catheter only partially obstructs thenostril leaving adequate room for breathing through the nose. However, the inert tracer gas could be injected into an endotracheal tube with the same results. The injection takes place early enough in the inspiratory phase of the respiratory cycle so that substantially all of the tracer gas is evenly distributed in the inspired air and carried into the alveolar compartment of the lungs, leaving essentially no tracer gas in the anatomical dead space at end inspiration.

Various parameters may be used to determine the phase of the inspiratory cycle during which helium will be injected. Preferably this will occur early in the cycle near the onset of inspiration. For example, a flow meter may be used to detect maximum flow of inspired air during which period the desired amount of tracer gas is injected. The inert gas may also be injected during a predetermined portion or percentage of the inspiratory cycle. For example, injection may begin ten percent of the way into the cycle and terminate sixty percent of the way through the cycle. Since a microprocessor or similar computing unit will be used as a controller the projected timing of a current cycle may be taken as the average over the last five or ten cycles. The timing is constantly upgraded by adding the cycle just completed and deleting the most distant cycle in making the computation. The amount of helium injected may vary from patient to patient depending on variables such as size and breath rate.

The exact interval of helium injection will be chosen such that the distribution of the helium tracer gas will be proportional to the distribution of ventilation. After several breaths a steady state condition is reached in which the amount of helium tracer being injected per breath equals the amount expired per breath. The amount of helium, ($V_{EHe}$), which is monitored, is equal to the nominal alveolar ventilation ($V_A$) times the alveolar concentration of helium ($F_{AHe}$) as shown by the following equation:

$$V_{EHE} = V_A F_{AHe} \quad (1)$$

When measured over a given time period having a known number of helium tracer injections the alveolar ventilation ($V_A$) can be measured by the following equation:

$$\dot{V}_{EHe} = \dot{V}_A F_{AHe} \quad (2)$$

Since values $V_{EHe}$ or $\dot{V}_{EHe}$ are known and $F_{AHe}$ can be directly obtained from an analysis of the alveolar gas, $V_A$ and $\dot{V}_A$ can be quickly determined.

Assuming the $CO_2$ content in inspired air is zero, $CO_2$ production is a product of alveolar ventilation ($\dot{V}_A$) and alveolar concentration of $CO_2$($F_{ACOdi\,2}$):

$$\dot{V}_{CO2} = \dot{V}_A F_{ACO2} \quad (3)$$

With $CO_2$ concentration being constantly monitored and alveolar ventilation being known the carbon dioxide production may be easily determined.

Oxygen consumption requires the knowledge of the oxygen concentration in both ambient or inspired and expired air. Since all gas exchange takes place in the alveoli oxygen consumption ($\dot{V}_{O2}$) may be generally stated to be the product of alveolar ventilation ($\dot{V}_A$) and the difference between the inspired oxygen concentration ($F_{IO2}$) and alveolar oxygen concentration ($F_{AO2}$):

$$\dot{V}_{O2} = \dot{V}_A (F_{IO_2} - F_{AO_2}) \quad (4)$$

However, due to the difference between inspired versus expired alveolar volume caused by gas exchange in the alveoli the measurement for $V_{O2}$ requires that the concentration of oxygen and carbon dioxide in both inspired air ($F_{IO2}$, $F_{ICO2}$) and alveolar air ($F_{AO2}$, $F_{ACO2}$) be monitored. Oxygen consumption is therefore determined according to the equation:

$$\dot{V}_{O2} = \dot{V}_A \left( F_{IO2} \frac{1 - F_{AO2} - F_{ACO2}}{1 - F_{IO2} - F_{ICO2}} - F_{AO2} \right) \quad (5)$$

Since carbon dioxide concentration in the inspired air ($F_{ICO2}$) is generally negligible that term may often be dropped from the equation without significantly altering the accuracy of the determination. It will be recognized that (1-$F_{AO2}$-$F_{ACO}$) is equivalent to the nitrogen concentration ($F_{AN2}$) in the alveolar gas and (1-$F_{IO2}$-$F_{ICO2}$) is equivalent to the nitrogen concentration ($F_{IN2}$) in the inspired air. Thus the oxygen fraction of inspired air is modified by the ratio of alveolar nitrogen to inspired nitrogen fractions.

In the above equation ($F_{AO2}$ and $F_{ACO2}$ may be determined from the same alveolar gas sample and $F_{IO2}$ and $F_{ICO2}$ (if needed) may be obtained from ambient air surrounding the patient.

The hardware required for carrying out the method of determining alveolar ventilation, carbon dioxide production and oxygen consumption in a patient is not limited to any one particular device. Various patents claim apparatus and methods for sampling and analyzing alveolar or end tidal air. U.S. Pat. Nos. 3,613,665; 3,661,528 and 3,910,261 are representative. A gas dispensing means suitable for injecting the proper amount of helium into the airway of a patient is taught in U.S. Pat. 4,062,313. A system for collecting alveolar gas samples via a catheter inserted into the nostril of a patient is disclosed by Farr, Doctoral Thesis "An Automated System for Measuring Alveolar-Arterial Oxygen and Carbon Dioxide Gradients in Infants" University of Utah, Dec. 10, 1974.

Since it is the arrangement of the system and the method of determining alveolar ventilation, carbon dioxide production and oxygen uptake that are considered to be novel, and not the use of any particular piece of equipment, the invention will be described in terms of a block diagram as represented in FIG. 1.

The patient interface may consist of a miniature nosepiece represented by block 10 consisting of two small-diameter plastic tubes or catheters extending a short distance into each naris supported by a small nose clip and a rubberized cloth band. The nosepiece 10 will be essentially non-occlusive and leads to the remainder of the gas insertion and sampling equipment. One plastic tube 11 leads from the nosepiece to a tracer gas insertion system 12 such as disclosed in U.S. Pat. No. 4,062,373. The other tube 13 interconnects the nosepiece 10 with a gas collection system 14. A small temperature sensitive thermistor placed at the end of one of the plastic tubes in one naris is electrically connected to a conventional microprocessor 15 or similar controller by line 16. The microprocessor 15 is electrically connected by line 17 to the tracer gas insertion system 12 and by line 18 to gas collection system 14. The gas collection system 14 may be connected to a gas analyzer 19 by a line 20. In the alternative the gas to be analyzed could be removed from gas collection system 14 by a syringe or other suitable means and injected into gas analyzer 19 which may be a mass spectrometer, gas chromatograph or other piece of equipment normally used in analyzing gas samples. The results obtained at the gas analyzer 19 can be relayed to a remote terminal 21 and into a computer 22 which determines alveolar ventilation, carbon dioxide production and oxygen uptake and visually records this data at printer 23.

Various parameters are available for determining when to start sampling during expiration in order to obtain maximum alveolar or end-tidal air. Some of these are referred to in the above mentioned patents and thesis. Since alveolar air is expelled during the latter part of the expiratory cycle a timed delay after the detection of the onset of inspiration may be used. Thus, if sampling of alveolar air is determined to occur over the last sixty, forty, etc. percent of the expiratory cycle, a microprocessor can be programmed to average expiratory times of the last x cycles (five, ten, etc.) and begin sampling at the desired point after the onset of inspiration as predetermined by the average time of the preceding cycles. Other variables such as flow rate, temperature, carbon dioxide, oxygen and inert tracer gas concentrations tend to plateau or reach a constant slope if flow rate temperature or concentration is plotted against time during expiration of alveolar air. Any of these variables may be sensed by fast responding means such as thermistors and sensitive electrodes and used as the parameter to indicate the start of sampling alveolar or end-tidal air. Sampling can be immediately stopped upon the detection of inspiration.

The invention will be described in connection with the use of a temperature responsive thermistor as described in Farr's above cited thesis keeping in mind that other systems as indicated could also be used.

At the onset of inspiration the thermistor will be cooled by inspired air sending a signal to the microprocessor 15 via line 16. During expiration the thermistor is warmed by the exhaled air again sending a signal via line 16 to the microprocessor 15.

In operation of the system the thermistor detects the onset of inspiration and sends a signal via line 16 to microprocessor 15 which in turn closes the gas sampling means and actuates the helium insertion system 12 via line 17 at the predetermined time thereby sending a known amount of helium through plastic tube 11 to nosepiece 10. The helium is inserted into the respiratory airstream appropriately near the beginning of each inspiratory phase such that all of the helium is carried into the alveoli. The amount of helium inserted is controlled by the microprocessor and is a product of the flow rate and operating time. After the preselected amount of helium has been inserted an electronic delay circuit actuates a valve in the helium insertion system thereby shutting off the helium flow. The response time for opening and closing the helium feed lines can be vary rapid being on the order of 1 to 5 milliseconds.

The onset of the expiratory cycle is noted at the thermistor by the rise in temperature created by expired gases and relayed via line 16 to the microprocessor 15. Since alveolar or end tidal air is expelled during the latter part of the expiratory cycle the microprocessor 15 is set to actuate the gas collection system 14 during said period as previously indicated. By whatever method is chosen the microprocessor 15, at the predetermined time, actuates the gas collection means 14 via line 18 and sampling of alveolar gas begins. Alveolar gas is drawn through tube 13 into the gas collection system 14 which may consist of a syringe pump operated by a stepping motor (IMC Magnetics). This motor can start, stop or reverse within 0.4 milliseconds. By this means, exact control of gas sample volume is controlled by the pump itself. The only valving necessary between the pump and the patient is a two way low volume valve for routing collected alveolar gas from the pump to the analyzer 19 or to a collection vessel. With the almost instantaneous reversibility of the pump, sampling can continue until the onset of inspiration is detected by the thermistor whereupon the pump can be reversed to expel the last part of air contained in tube 13 which could be contaminated with a minor amount of inspirted air. Thus sampling can continue throughout the entire latter part of the expiration cycle.

In order to obtain $\dot{V}_{EHe}$ gas, samples from several cycles are obtained. When the gas collection means has collected a predetermined volume of alveolar gas over a predetermined number of cycles the gas is fed to a mass spectrograph 19 or other analyzer via line 20 or is collected separately for injection into a gas analyzer. In the gas analyzer the helium fraction ($F_{AHe}$), CO$_2$ fraction ($F_{ACO_2}$) and oxygen fraction ($F_{AO_2}$) are determined and the monitored data is used to ascertain the alveolar ventilation ($\dot{V}_A$). The $\dot{V}_A$ along with the monitored carbon dioxide and oxygen fractions of alveolar air and the fraction of oxygen in inspired air ($F_{IO_2}$), which is also monitored, enables the determination of carbon dioxide production and oxygen uptake.

Preferably the signals obtained at the mass spectrograph or other analyzer 19 are fed via a remote terminal 21 into a computer 22 for resolution and determination of alveolar ventilation, carbon dioxide production and oxygen uptake. These determinations are visually printed out at printer 23.

As previously mentioned a steady state condition must be reached wherein the rate of helium injection equals the amount of helium expired before valid sampling can begin.

Alveolar ventilation, carbon dioxide production and oxygen uptake may be monitored continuously or intermittently as required.

While a particular embodiment of the invention has been given, numerous additional modifications and variations are possible in view of the above teachings. It is therefore intended that the scope of the invention be limited only in and by the terms of the appended claims.

I claim:

1. A method of sampling and analyzing alveolar air in a human subject without requiring an air-tight seal between the subject and the monitoring equipment to determine alveolar ventilation, carbon dioxide production and oxygen uptake comprising the steps of;
   (a) determining the onset of inspiration,
   (b) directly introducing a known amount of an inert tracer gas into the airway of the patient by non-airtight catheter means during inspiration such that the inert tracer gas is distributed in the inspired air and is carried to the alveoli, leaving essentially no tracer gas in the anatomical dead space,
   (c) determining the onset of expiration of alveolar air and directly sampling a portion of alveolar air by a non-airtight catheter means and monitoring the inert gas concentration of a portion of the alveolar air stream by non-airtight means,
   (d) repeating cycles (b) and (c) until a steady state in the concentration of inert tracer gas is reached,
   (e) continuing cycles (b) and (c) and monitoring the oxygen and carbon dioxide concentrations in the portion of the alveolar air stream at steady state inert tracer gas concentrations, and,
   (f) determining the alveolar ventilation, carbon dioxide production and oxygen uptake from the monitored inert tracer gas, carbon dioxide and oxygen values.

2. A method according to claim 1 wherein the monitoring of the inert tracer gas, carbon dioxide and oxygen concentrations and the addition of inert tracer gas into the airway of the patient creates electronic signals which are fed into translation means which convert said electronic signals into visual values showing alveolar ventilation, carbon dioxide production and oxygen uptake.

3. A method according to claim 2 wherein the inert tracer gas is substantially insoluble in blood.

4. A method according to claim 3 wherein the inert tracer gas is helium.

5. A method according to claim 3 wherein the inert tracer gas is introduced into a nostril of the subject.

6. A method according to claim 5 wherein the portion of the alveolar air stream is removed from a nostril of the subject.

7. A method according to claim 3 wherein the inert tracer gas is introduced into and the portion of the alveolar air stream is removed from an endotracheal tube in the trachea of the subject.

8. A method according to claim 3 wherein the inert tracer gas is inserted into the airway of a patient at a fixed time interval after the onset of inspiration.

9. A method according to claim 8 wherein the inert tracer gas in inserted into the airway of a patient at a time interval after the onset of inspiration which time interval is a fixed fraction of the running average of the inspiratory period.

10. A method according to claim 3 wherein the inert tracer gas in introduced into the airway of a subject during maximum inspiratory air flow.

11. A method according to claim 3 wherein the onset of alveolar air expiration is determined by a plateau in the temperature of expired air.

12. A system suitable for determining alveolar ventilation, carbon dioxide production and oxygen consumption comprising,
   (a) means which do not require an airtight seal to a patient adapted to supply a known amount of an inert tracer gas into the airway of a patient during inspiration,
   (b) sampling means which do not require an airtight seal to a patient adapted to withdraw a portion of expired alveolar air stream from the airway of a patient,
   (c) actuator means adapted to sense the onset of inspiration in a patient and immediately terminate operation of said sampling means in response thereto and to initiate operation of said inert tracer gas supplying means at a predetermined time relative to the onset of inspiration,
   (d) actuator means adapted to sense the onset of expiration and to initiate operation of said sampling means at a time subsequent to the onset of expiration according to a predetermined sensed parameter,
   (e) means for analyzing gas collected from said sampling means and from ambient air,
   (f) means for supplying gas from said sampling means and from ambient air to said analyzing means,
   (g) means connected to said analyzing means adapted to receive signals from said analyzing means and to translate said signals into visual results indicating alveolar ventilation, carbon dioxide production and oxygen uptake.

13. A system according to claim 12 wherein the means for analyzing gas from said sampling means is a gas chromatograph.

14. A system according to claim 12 wherein the means for analyzing gas from said sampling means is a mass spectrometer.

15. A system according to claim 12 wherein the actuator means adapted to sense the onset of inspiration and the onset of expiration are temperature responsive.

16. A system according to claim 15 wherein the sampling means includes a catheter adapted to be inserted into, but not block, a nostril of a patient.

17. A system according to claim 16 wherein the inert tracer gas means includes a catheter adapted to be inserted into, but not block a nostril of a patient.

* * * * *